(12) United States Patent
Zaidi et al.

(10) Patent No.: US 11,395,915 B2
(45) Date of Patent: Jul. 26, 2022

(54) ELECTRODE DEVICES AND METHODS OF MANUFACTURING

(71) Applicant: GALVANI BIOELECTRONICS LIMITED, Brentford (GB)

(72) Inventors: Faisal Zaidi, Brentford (GB); Sebastien Ouchouche, Brentford (GB)

(73) Assignee: Galvani Bioelectronics Limited, Brentford (GB)

( * ) Notice: Subject to any disclaimer, the term of this patent is extended or adjusted under 35 U.S.C. 154(b) by 226 days.

(21) Appl. No.: 16/634,626

(22) PCT Filed: Jul. 23, 2018

(86) PCT No.: PCT/GB2018/052075
§ 371 (c)(1),
(2) Date: Jan. 28, 2020

(87) PCT Pub. No.: WO2019/020984
PCT Pub. Date: Jan. 31, 2019

(65) Prior Publication Data
US 2021/0085965 A1   Mar. 25, 2021

Related U.S. Application Data

(60) Provisional application No. 62/538,387, filed on Jul. 28, 2017.

(51) Int. Cl.
*A61N 1/05* (2006.01)
*A61N 1/375* (2006.01)
*A61N 1/36* (2006.01)

(52) U.S. Cl.
CPC ......... *A61N 1/0558* (2013.01); *A61N 1/0556* (2013.01); *A61N 1/37518* (2017.08); *A61N 1/36185* (2013.01)

(58) Field of Classification Search
CPC ............... A61N 1/0558; A61N 1/0556; A61N 1/37518; A61N 1/36185; A61N 1/0551
See application file for complete search history.

(56) References Cited

U.S. PATENT DOCUMENTS 4,573,481 A * 3/1986 Bullara ............... A61N 1/0556
607/118
5,003,992 A 4/1991 Holleman et al.
(Continued)

FOREIGN PATENT DOCUMENTS

EP    0865800 A2   9/1998
EP    1935448 A1   6/2008
(Continued)

OTHER PUBLICATIONS

International Preliminary Report on Patentability for Application No. PCT/GB2018/052074, dated Jan. 28, 2020, 6 pages.
(Continued)

*Primary Examiner* — Eugene T Wu
(74) *Attorney, Agent, or Firm* — Patterson Thuente Pedersen, P.A.

(57) ABSTRACT

An extravascular or intravascular neural interface is disclosed containing electrodes for neurostimulation of the vessel. The devices are housed in flexible substrates formed from a multilumen tubing housing conductors for electrodes positioned in a distal serpentine shaped end of the device. The distal serpentine shaped end includes rows or strips of electrodes or coil electrodes.

11 Claims, 4 Drawing Sheets

(56) References Cited

U.S. PATENT DOCUMENTS

| | | | |
|---|---|---|---|
| 6,181,971 B1 | 1/2001 | Doan | |
| 6,292,703 B1 | 9/2001 | Meier et al. | |
| 7,676,275 B1 * | 3/2010 | Farazi | A61N 1/0551 607/127 |
| 8,155,757 B1 | 4/2012 | Neisz et al. | |
| 8,515,520 B2 | 8/2013 | Brunnett et al. | |
| 2006/0041277 A1 | 2/2006 | Deem et al. | |
| 2007/0106340 A1 * | 5/2007 | Bolea | A61N 1/36125 607/44 |
| 2008/0103545 A1 | 5/2008 | Bolea et al. | |
| 2010/0268311 A1 | 10/2010 | Cardinal et al. | |
| 2012/0022617 A1 | 1/2012 | Tockman et al. | |
| 2013/0150933 A1 | 6/2013 | Pianca et al. | |
| 2013/0289686 A1 | 10/2013 | Masson et al. | |
| 2014/0188202 A1 | 7/2014 | Zarembo et al. | |

FOREIGN PATENT DOCUMENTS

| | | | |
|---|---|---|---|
| WO | WO-2008048471 A2 | 4/2008 | |
| WO | WO-2009135075 A1 | 11/2009 | |
| WO | WO-2014018092 A1 | 1/2014 | |

OTHER PUBLICATIONS

International Preliminary Report on Patentability for Application No. PCT/GB2018/052075, dated Jan. 28, 2020, 8 pages.
International Preliminary Report on Patentability for Application No. PCT/GB2018/052077, dated Jan. 28, 2020, 7 pages.
International Search Report and Written Opinion for Application No. PCT/GB2018/052075, dated Oct. 8, 2018, 11 pages.
International Search Report and Written Opinion for Application No. PCT/GB2018/052077, dated Oct. 15, 2018, 9 pages.
International Search Report for Application No. PCT/GB2018/052074, dated Nov. 6, 2018, 2 pages.
International Search Report for Application No. PCT/GB2018/052077, dated Oct. 15, 2018, 2 pages.

* cited by examiner

ELECTRODE DEVICES AND METHODS OF MANUFACTURING

PRIORITY CLAIM

The present application is a National Phase entry of PCT Application No. PCT/GB2018/052075, filed Jul. 23, 2018, which claims priority from U.S. Provisional Application No. 62/538,387, filed Jul. 28, 2017, each of which is hereby fully incorporated herein by reference.

BRIEF DESCRIPTION

The present disclosure is related to embodiments of extravascular and intravascular devices containing electrodes neurostimulation of a vessel. The devices are housed in flexible substrates formed from a multilumen tubing housing conductors for electrodes positioned in a distal serpentine shaped end of the device. The distal serpentine shaped end includes rows or strips of multiple electrodes or coil electrodes. The device may be positioned inside a target vessel (i.e. intravascular) or around a target vessel (i.e. extravascular).

BACKGROUND

Electrical devices of various shapes and sizes including one or more electrodes have been used for neurostimulation of target anatomy for years. U.S. Pat. Pub. No. 2008/0183264 discloses extravascular devices having a variety of shapes that are designed to place electrodes at different points along the interior walls of a target vessel for neurostimulation, including various spiral or serpentine shaped designs. U.S. Pat. Pub. No. 2008/0183265 discloses some of the same designs and electrical conductors for such devices having improved retention when placed within a jugular vein. Additional spiral configurations for intravascular electrodes are disclosed in U.S. Pat. Pub. No. 2013/0289686.

Each of the above examples illustrate a variety of existing spiral or serpentine-like designs that can be used for intravascular treatment that are more rigid in nature and lack radial flexibility and self-sizing capabilities. If the nerves in the walls of the target vessel are excessively compressed by the device, nerve damage may result from the decreased blood flow and constricted nerve fibers. Temporary swelling of the vessel caused by the trauma of the positioning of the device can exacerbate such nerve damage. In contrast, loose fitting devices can result in poor electrical contact and low treatment efficiency, which can further degrade over times as a result of ingrowth of connective tissue between the target vessel and the device.

While conventional helical, spiral or serpentine electrode devices permit some radial expansion that helps with post-positioning edema or swelling of the target vessel, more fluid exchange with surrounding tissue, better electrical contact, and reduced growth of connective tissue. Helical, spiral or serpentine devices, however, require a complex positioning effort that requires significant dissection and nerve manipulation in order to wind the helix around the nerve at least two times. Positioning of such devices also requires mobilization of a large portion of the nerve because the cathode and anode electrodes are typically positioned by their own device.

Further, helical, spiral or serpentine devices are usually manufactured by over-molding the electrodes in a helically shaped silicone substrate and gluing the structure to a silicone-based conductor body. Such a manufacturing method is complex and results in a device having limited tensile strength, due to limitations in the strength of the bonds, and is not well suited for multipolar applications.

SUMMARY

In one aspect of the disclosure there is a neural interface for interfacing with a target vessel, the neural interface comprising: a tube including a plurality of lumina within the tube and having a helical shape along at least part of its distal length; a plurality of conductors, wherein each conductor among the plurality of conductors is inserted into a corresponding lumen; at least two electrodes, wherein each electrode among the at least two electrodes is connected to a first end of a corresponding conductor and positioned at a position along the length of the tube so as to form no electrical transverse gap between electrodes over at least a 360 degree turn around an interior surface or an exterior surface of the target vessel when positioned in or on the target vessel; and an overlay positioned over the tube and the electrodes, the overlay including a plurality of openings exposing each conductor to the interior surface or the exterior surface of the target vessel.

In the neural interface, the positioning of the electrodes along the length of the tube forms no electrical transverse gap between electrodes over at least a 360 degree turn around an interior surface or an exterior surface of a target vessel when positioned in or on the target vessel. In other words, when the neural interface is positioned on the target vessel there is no longitudinal axis/plane along the length of the interior or exterior surface of the target vessel that does not pass through an electrode over at least a 360 degree turn around an interior surface or an exterior surface of a target vessel. This may ensure complete electrical coverage (360° circumferential coverage) of the target vessel over a length of the target vessel.

The neural interface may be configured to provide at least one open path or gap for the target vessel when positioned in or on the target vessel. In other words, the neural interface forms at least one portion where the tube is not present in or on the target vessel. This open structure ensures that the target vessel may pulsate without a complete 360° circumferential constriction and that an initially swollen target vessel can return to a normal state over time without constriction of the target vessel when it is swollen and without losing electrode to target vessel contact when the target vessel is in its normal state.

The tube of the neural interface may be made from a flexible material. This flexible material may be non-rigid and capable of elastic deformation (i.e. reversible deformation). Thus, the tube may be biased along its length to form a coiled shape. In this way, tube may have an initial resting configuration and can be displaced from the initial resting state into a different state in order to position the interface with respect to the target vessel. Then, when the neural interface is in an appropriate position the interface can be released allowing the tube to be urged back to its resting state, thus softly gripping the target vessel. This can also allow the neural interface to be positioned in a simple and convenient manner. In addition, this can ensure good contact between the electrodes and the target vessel, without constricting the target vessel.

The neural interface may be configured to be positioned around the outside of a target vessel (i.e. extravascular). In this example, the tube may be biased towards a contracted configuration. Thus, the tube can be expanded when positioning the interface around the target vessel. However, when the tube is released, the tube is urged towards the contracted configuration which grips the target vessel.

The neural interface may be configured to be positioned on the inside of a target vessel (i.e. intravascular). In this example, the tube may be biased towards an expanded configuration. Thus, the tube can be contracted when positioning the interface in the target vessel. However, when the tube is released, the tube is urged towards the expanded configuration which grips the target vessel by forcing itself outwards onto the interior surface of the target vessel.

In another aspect of the disclosure there is a method of manufacturing a neural interface, comprising: (a) laser ablating a plurality of cavities in an outer diameter of a tube including a plurality of lumina; (b) inserting a conductor into each lumen among the plurality of lumina; (c) connecting an electrode to a distal end of a conductor and positioning the electrode over a cavity among a plurality of cavities, wherein a first cavity among the plurality of cavities is near a proximate end of a length of the tube; (d) placing a spacer over the tube and positioning the spacer against a distal edge of the electrode; (e) repeating (c) and (d) until a last electrode among the plurality of electrodes is positioned in a corresponding last cavity; (f) melting the plurality of spacers and filling the plurality of cavities; (g) inserting an overlay over the distal length; and (h) thermoshaping the distal length in a helical shape.

In this way, the neural interface can be manufactured in a simple manner. In addition, the manufacturing method can strengthen the bonds between the components, thus improving the tensile strength of the neural interface. The manufacturing method is particularly advantageous for multipolar devices.

In the present disclosure, a vessel refers to a vessel and a nerve (or nerves) that travels along with the vessel. The vessel may be an artery (or arteries) and/or a vein (or veins) and/or a lymph vessel (or lymph vessels). A nerve that travels along a vessel may be a nerve that is adjacent to the vessel or a nerve that is in the vicinity of the vessel.

In the present disclosure, a target vessel may be a target vessel that includes a nerve (or nerves) that travels along with the vessel. The target vessel may be an artery (or arteries), and/or a vein (or veins), and/or a lymph vessel (or lymph vessels).

DETAILED DESCRIPTION

The present disclosure is related to embodiments of multipolar extravascular and intravascular neural interface devices containing electrodes for neurostimulation of the vessel. The devices are housed in flexible substrates formed from a multilumen tubing housing conductors for electrodes positioned in a distal serpentine shaped end of the device. The distal serpentine shaped end includes rows or strips of electrodes or coil electrodes. The device may be positioned inside or around a target vessel.

Figure 1:
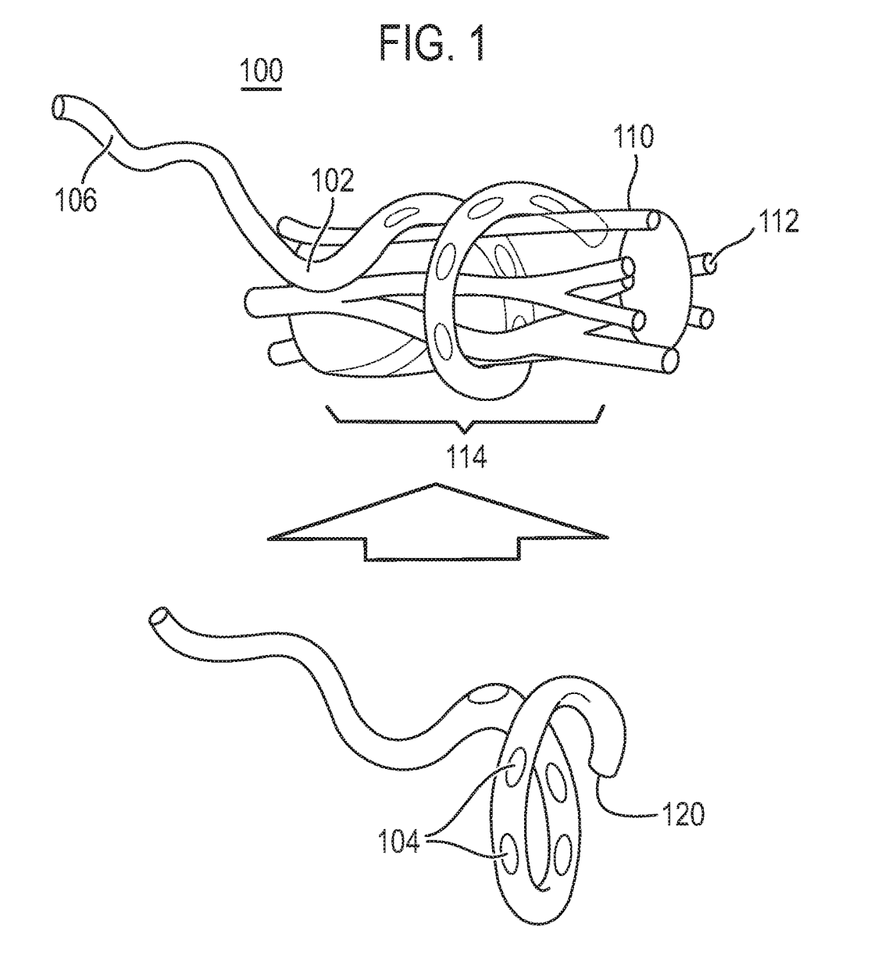
FIG. 1 is a perspective view of an embodiment of an extravascular electrode device including a flexible serpentine structure for holding the electrodes and positioning the device.

An embodiment of an extravascular neural interface in accordance with the present disclosure is illustrated in FIG. 1. The neural interface 100 may comprise a serpentine clasp, including a supporting substrate 102, manufactured of silicone or a similar flexible substance. In embodiments further discussed below, the supporting substrate 102 may be formed of polyurethane multilumen tubing with a silicone overlay and other supporting structure. Other materials may also be used for the tubing, such as styrene isoprene butadiene (SIBS), polyamide, parylene, liquid-crystal polymer (LCP), polytetrafluoroethylene (PTFE), polyethylene (PE), polypropylene (PP), fluorinated ethylene propylene (FEP), ethylene-tetrafluoroethylene (ETFE), polyurethane, or another biocompatible polymer.

The neural interface 100 may include a plurality of electrodes or electrode arrays 104 spaced along a length of the spiraled distal end of the neural interface 100. The electrodes 104 may be multiple platinum or platinum alloy electrodes (or electrode arrays), such as thin metal sheets, segmented metal contact, thin-film based, or other types of electrodes or electrode arrays. The electrodes 104 may be wired to a controller through conventional conductors 106, such as 35N LT® DFT (Drawn Filled Tubing) with a 28% Ag core, in a stranded cable configuration (e.g., 7×7), or in a multi-filar coil configuration.

The neural interface 100 may be positioned so as to be wrapped around the exterior walls of a target vessel 110 having a number of nerves 112 extending through the walls. The neural interface may be biased along a distal length 114 to form a coiled shape as illustrated in FIG. 1 when in its natural position. Yet, the neural interface 100 may also be sufficiently compliant that the neural interface 100 may be straightened sufficiently to place the neural interface 100 in a catheter (not shown). The distal end of the catheter may then be positioned using known techniques so the distal end 120 of the neural interface 100 is placed at designed location along the target vessel 110. Once the distal end 120 is positioned, the catheter may be withdrawn. As the catheter withdraws, the distal length 114 of the neural interface 100 will coil around the target vessel 110 as distal length 114 returns to its natural position.

Although the neural interface 100 coils around the target vessel 110, the neural interface 100 is configured to maintain an open structure, such that no portions form a closed circumscribed circle at any point along a length of the target vessel. In other words, no closed circle covering 360 degrees of an orthogonal portion of the target vessel's length is formed by the structure. This may serve to insure that the target vessel may pulsate without a complete 360° circumferential constriction and that an initially swollen target vessel can return to a normal state over time without constriction of the target vessel when it is swollen and without losing electrode to target vessel contact when the target vessel is in its normal state. In an embodiment, the neural interface 100 may be wound around the target vessel at least one turn and may be wound additional turns. As shown in FIG. 1, the neural interface 100 may be designed for an extravascular application, so the electrodes 104 may be positioned along an interior surface area of the neural interface that will be in contact with the target vessel 110.

An electrode design that employs one or more electrode strips may make it possible to maximize electrode coverage while minimizing the conductor interconnection process, such as through laser welding, resistance welding, etc. However, to minimize the rigidity of the electrode, i.e., making it sufficiently flexible, the electrode may have to be very thin (typically between 25 um and 50 um), which may make the interconnection of the conductors to the electrodes more challenging, also, to keep the electrode as flexible as possible, surface features may not be possible to add to the electrode as it would decrease the electrode flexibility. For this reason, an electrode may be recessed within the substrate material, with silicone rims or silicone webbing that may serve to hold the electrode in place. However, recessing the electrode may potentially decrease the efficacy of the stimulation.

On the other hand, "segmented" electrode designs may provide better mechanical compliance, create the possibility of surface features, i.e., protruding electrodes, and make it possible to control each electrode individually (i.e., current steering). The trade-offs include limited electrode coverage, increased interconnection processes, decreased retention force. In addition, segmented electrodes provide increased flexibility to the neural interface, thereby making it possible open the neural interface with a deployment tool wider and for a longer period of time, without creating excessive stress on the electrodes, than might be possible with a single thin electrode. In addition, connecting individual electrodes or different arrays of electrodes to different conductors may enable selective stimulation of the target vessel by individually controlling each connected device. For example, individual electrodes, if wired separately, may be selected and activated for power/current grading of a stimulation field of the target vessel.

Figure 2:
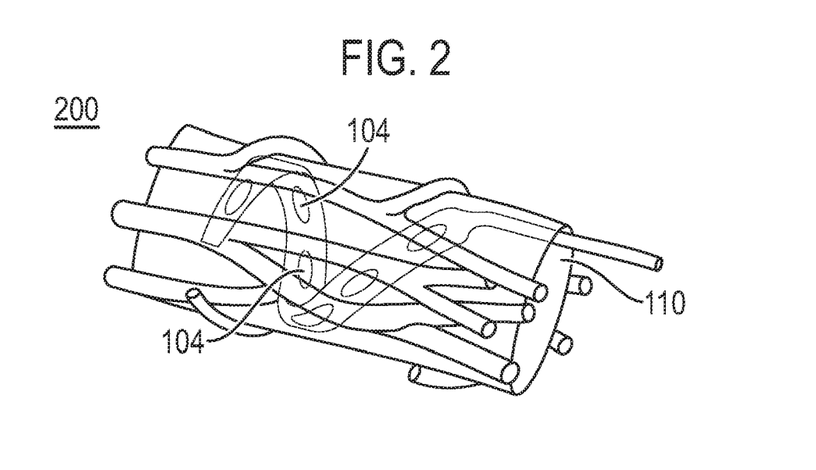
FIG. 2 is a perspective view of an embodiment of an intravascular electrode device including a flexible serpentine structure for holding the electrodes and positioning the device.

The neural interface 200 of FIG. 2 may be substantially the same as neural interface 100, but neural interface 200 may be designed for an intervascular application so the electrodes 204 may be positioned along an exterior surface area (lumen wall) of the neural interface so as to make good contact with the interior walls of the target vessel 110. Depending on the location of the target vessel, the procedure for positioning the neural interface 200 may be minimally invasive. For example, for positioning in a splenic artery, the procedure may be performed through a total percutaneous access via standard (e.g., femoral) artery access. Once the catheter (not shown) is positioned for deployment of the neural interface 200, the catheter may be withdrawn and the released neural interface will self-size to the inside of the target vessel 110, which requires the distal length to be formed so its normal relaxed position will cause the spiral to expand so as to make good contact with the interior walls of the target vessel 110.

The winding of the neural interface 100 around the target vessel 110 is a soft self-sizing that ensures good contact is made between the surface of the substrate and the surface of the target vessel 110. This also serves to ensure that this is good electrical contact between the electrodes 104 and the nerves 112, but without excessive compression of the nerves 112 or the target vessel 110 (i.e., reduced blood flow). The self-sizing configuration of the neural interface 100 may enable the neural interface to accommodate anatomical variability, may better accommodate radial expansion of the nerve/vessel as a result of post-positioning edema or swelling, and may accommodate the pulsatile behavior of arteries. The naturally open structure of the spiral of the neural interface 100 prevents a complete 360° circumferential constriction at any point, which may promote open trench for easy pulsation and more normal fluid and nutrient exchange with the intervention site and surrounding tissue. This may also help to minimize growth of connective tissue between the electrode nerve/vessel interfaces.

Figure 3:
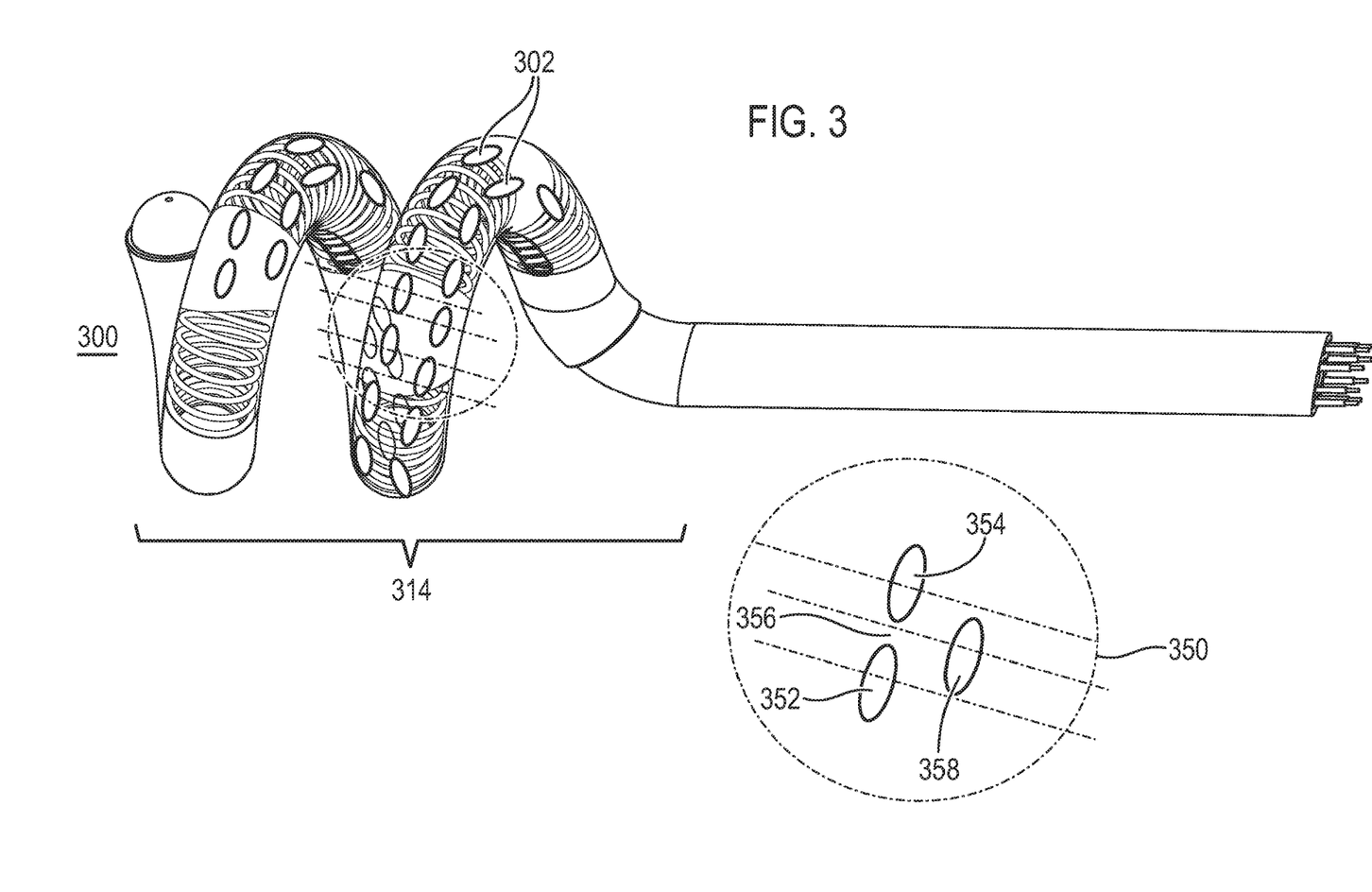
FIG. 3 is a perspective view of an embodiment of an intravascular electrode device including rows of multiple contact electrodes.
Figure 4:
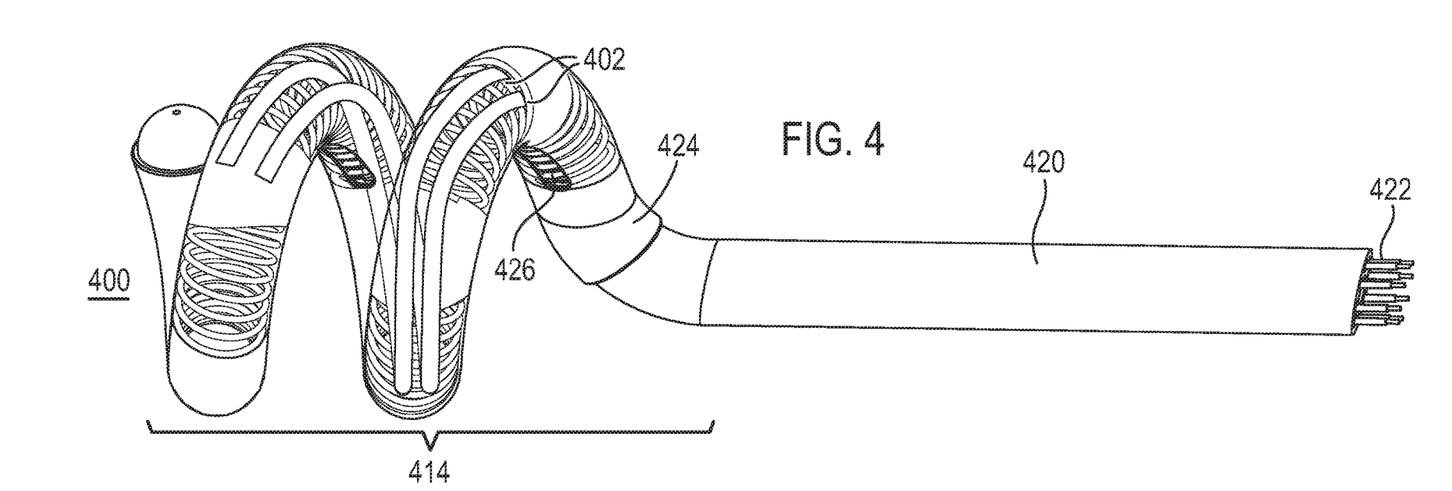
FIG. 4 is a perspective view of an embodiment of an intravascular electrode device including continuous strips of electrodes.
Figure 5:
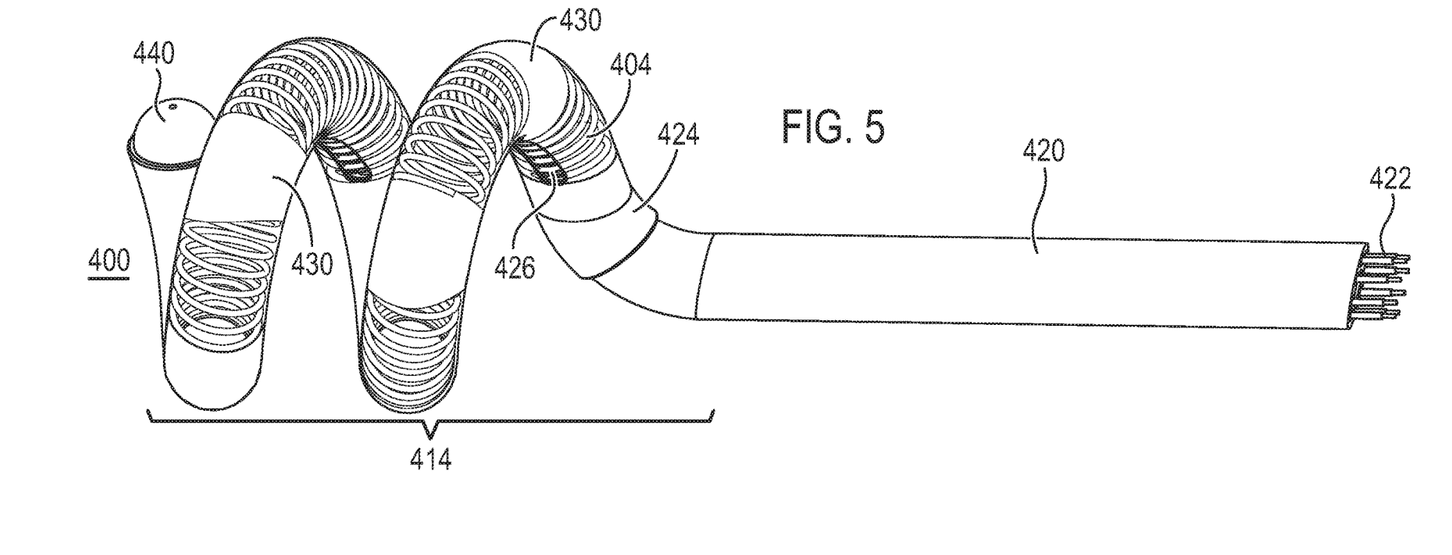
FIG. 5 is a perspective view of an embodiment of an electrode device illustrating a manufacturing method.

FIGS. 3, 4, 6 and 7 provide a more detailed description of embodiments of spiral neural interfaces 300, 400, 600 and 700, respectively, in accordance with the present disclosure. The neural interfaces 300, 400, 600 and 700 may be essentially the same, but for the electrodes and whether the electrodes are arranged for an intravascular application (neural interfaces 300 and 400) or arranged for an extravascular application (neural interfaces 600 and 700). In FIGS. 3 and 5, the electrodes 302 may be multiple positive rows and multiple negative rows of multiple contact electrodes arranged at a surface of the distal length 314 so as to cover at least one complete helical turn (360°) of the spiral of the neural interface 300. The contacts of the electrodes 302 may be arranged on a surface of the substrate to be adjacent to an exterior surface of the target vessel for an extravascular design, as shown in FIG. 3, and on a surface of the substrate to be adjacent to an interior surface of the target vessel for an intravascular design, as shown in FIG. 5. All of the electrodes in a first strip of electrodes 302 may have a negative polarity while all of the electrodes in a second strip of electrodes 302 may have a positive polarity, or the negative and positive polarity may be mixed within a single strip of electrodes 302. In other words, the polarity of any electrode can be determined by a controller (not shown) providing power to the electrode and is not necessarily dependent on a mechanical structure of an electrode to determine that electrode's polarity. Nevertheless, the electrodes can be configured to have a specific polarity and configured for that polarity to be changed. For example, an electrode could be configured to have a selective negative polarity, i.e., negative polarity is selected, and then be configured, at a later point in time, to have a selective positive polarity.

Figure 6:
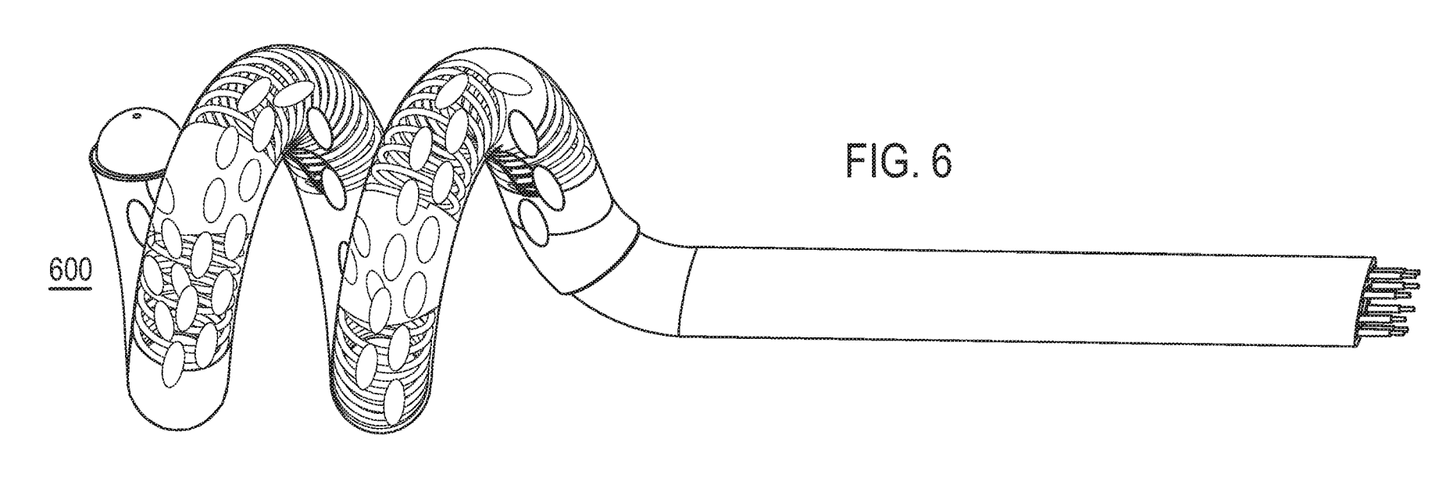
FIG. 6 is a perspective view of an embodiment of an extravascular electrode device including rows of multiple contact electrodes.
Figure 7:
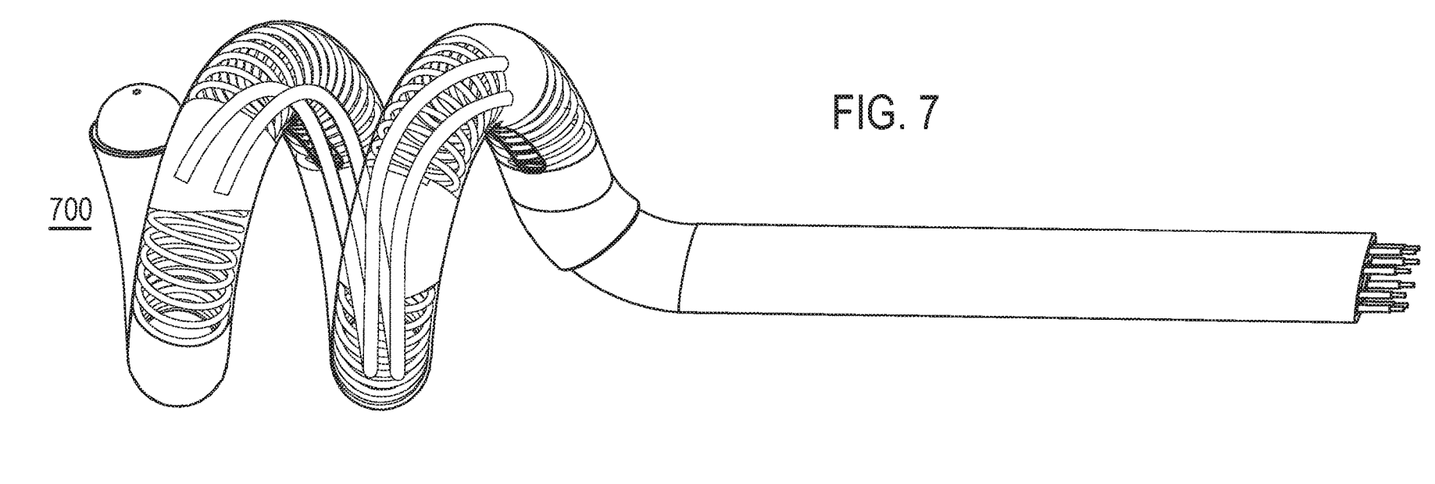
FIG. 7 is a perspective view of an embodiment of an extravascular electrode device including continuous strips of electrodes.

The contacts of the electrodes 302 may be positioned in an overlapping fashion, such that no electrical transverse gaps are created between the contacts of the rows of electrodes 302. In FIGS. 4 and 6, the electrodes 402 may be multiple positive continuous strip and multiple negative continuous strips of electrodes arranged at the surface of the distal length 14 so as to cover at least one complete helical turn (360°) of the spiral of the neural interface 400, which naturally also prevent any transverse gaps between the strips. The electrodes 402 may be arranged on a surface of the substrate to be adjacent to an exterior surface of the target vessel for an extravascular design, as shown in FIG. 4, and on a surface of the substrate to be adjacent to an interior surface of the target vessel for an intravascular design, as shown in FIG. 6.

An "electrical transverse gap" refers to any gap between electrodes which extends along the longitudinal axis of the spiral neural interface, the longitudinal axis of the neural interface corresponding to a direction along the target vessel. In other words, an electrical transverse gap is formed on a circumference of the neural interface (the circumference formed when the neural interface is positioned on the target vessel) when the electrodes are aligned so that there is point along a line following the length of the interface where an electrode is not encountered. If a first set of segmented electrodes, each with a gap between it and any neighboring electrode, are positioned around the circumference, in order to eliminate any electrical transverse gap in the neural interface, a second set of segmented electrodes, each with a gap between it and any neighboring electrode, would need to be positioned next to the first set, along the length of the target vessel, such that each electrode in the second set is positioned adjacent to a gap formed in the first set, and vice versa, such that at no point along a line following the length of the target vessel where the neural interface is positioned, would at least one electrode would not cross the line. If the gaps between electrodes were bigger than the size of an electrode, additional sets of segmented electrodes could be utilized with each set staggered so as to prevent an electrical transverse gaps.

Aligning individual electrodes or arrays of electrodes so as to remove electrical transverse gaps, say between two rows of electrodes or some other arrangement, may insure complete electrical coverage (360° circumferential coverage) of the target vessel over a length of the target vessel. For example, as illustrated in the detailed circle 350, electrodes 352 and 354 are spaced apart to create a physical transverse gap 356, that lies side to side to the electrodes 352 and 354. However, by aligning electrode 358 at a position (staggered) between the position of electrodes 352 and 354, an electrical transverse gap is eliminated. As illustrated, a total of 8 coiled platinum electrode rows or strips may be utilized in each neural interface. Neural interfaces 300 and 400 may also be configured for intravascular applications by locating the electrodes along exterior surfaces of the neural interfaces 300 and 400.

While further reference herein is only made to neural interface 400, the structure of neural interfaces 100, 200, 300, 600 and 700 may be essentially the same. Neural interface 400 may be manufactured from a polyurethane multilumen tubing 420, such as octolumen tubing for an 8-polar electrode interface, plus one additional lumen for insertion of a stylet. The outer diameter of the multilumen tubing may be about 1.3 mm. The conductors 422 may be 35N LT® DFT 28% Ag stranded cable in a 7×7 configuration. An overlay 424 of thin and soft silicone may be placed over the distal length, with 8 laser ablated apertures 426 facing inward so as to enable good contact between the electrodes 402 and the surface of the target vessel.

With further reference to FIG. 5, a method of manufacturing the neural interface 400, with a series of coil electrodes versus rows or strips, is further described. The electrodes 404 may be platinum electrodes in the form of coils so as to provide desired flexibility. In accordance with an embodiment, the method may follow the steps of:

1. The outer diameter of the polyurethane multilumen tubing 420 is superficially laser ablated over approximately 15% of the outer diameter. This opens the outer surface and a sublumen (through which the conductors for the electrodes are inserted) so as to create appropriate cavities for each electrode and enabling each conductor to be connected to each electrode.

2. The conductors 422 are inserted into the lumen of the polyurethane multilumen tubing 420.

3. A coil electrode 404 is positioned at a cavity along the distal length 414 and laser welded to its conductor. The first electrode is positioned at the proximate end of the distal length 414.

4. A polyurethane spacer 430 is then inserted over the distal end of the neural interface and against the distal edge of the electrode.

5. Steps 3 and 4 are repeated until the last electrode is welded in place at the end of a spacer and the last spacer is in place.

6. The distal length 414 is then reflowed, melting the spacers and filling the laser ablated cavities.

7. The distal end 440 is then centerless grinded. Centerless grinding is a machining process that uses abrasive cutting to remove material from a workpiece.

8. The electrodes are microblasted to remove the excess polyurethane.

9. The silicone overlay tube 424 is solvent-swollen and inserted over the distal length 414.

10. The electrodes are exposed by laser ablating openings in the silicone overlay at desired locations.

11. The distal length 414 of the assembled neural interface 400 is helically thermoshaped around a mandrel of appropriate diameter and at an appropriate helix angle for its intended application.

The resulting neural interface 400 is self-sizing and thereby configured to accommodate anatomical variability at the intervention site of the target vessel. The resulting neural interface 400 is inherently compliant and thereby configured to accommodate pulsatile behavior in the target vessel. The resulting neural interface 400 has open structures that are configured to permit the passage of fluids and nutrients to the invention site. The resulting neural interface 400 is self-retaining.

The following is a non-exhaustive list of embodiments that may or may not be claimed:

1. A neural interface, comprising:
    a tube including a plurality of lumen within the tube and having a helical shape along a distal length;
    a plurality of conductors, wherein each conductor among the plurality of conductors is inserted into a corresponding lumen;
    at least two electrodes, wherein each electrode among the at least two electrodes is connected to a distal end of a corresponding conductor and positioned at a desired position along the distal length of the tube so as to form no electrical transverse gap between electrodes over at least a 360 degree turn around an interior surface or an exterior surface of a target vessel when positioned in or on the target vessel; and
    an overlay positioned over the tube and the electrodes, the overlay including a plurality of openings exposing each conductor to the interior surface or the exterior surface of the target vessel.

2. The neural interface of embodiment 1, wherein the plurality of electrodes are positioned toward a surface of the tubing adjacent to the interior surface of the target vessel.

3. The neural interface of embodiment 1, wherein the plurality of electrodes are positioned toward a surface of the tubing adjacent to the exterior surface of the target vessel.

4. The neural interface of embodiment 1, further comprising a plurality of spacers, wherein at least one spacer is positioned between adjacent electrodes among the plurality of electrodes.

5. The neural interface of embodiment 4, wherein the desired position is determined by a laser ablation in the surface of the tube, wherein the tube and the plurality of spacers are a polyurethane material, wherein the polyurethane material is reflowed to melt the spacers, fill the laser ablation and create a distal end for the tube.

6. The neural interface of embodiment 5, wherein the distal end is centerless ground.
7. The neural interface of embodiment 1, wherein the at least two electrodes are coil electrodes.
8. The neural interface of embodiment 1, wherein the overlay is a silicone-based material.
9. The neural interface of embodiment 8, wherein the silicone-based material is doped with a steroid drug.
10. The neural interface of embodiment 8, wherein the silicone-based material is coated with a hydrophilic polymer.
11. The neural interface of embodiment 1, wherein the helical shape includes at least one complete helical turn.
12. The neural interface of embodiment 1, wherein the desired position is determined by a laser ablation in the surface of the tube.
13. The neural interface of embodiment 1, wherein the at least two electrodes are a first continuous strip and a second continuous strip, wherein the first continuous strip is configured to have a negative polarity and the second continuous strip is configured to have a positive polarity.
14. The neural interface of embodiment 13, wherein the first continuous strip and the second continuous strip are embedded in the tube and recessed from the exterior surface of the tube.
15. The neural interface of embodiment 1, wherein the at least two electrodes are a first continuous strip, a second continuous strip and a third continuous strip, wherein at least two continuous strips are configured to have a first polarity and a remaining continuous strip is configured to have a second polarity, the first polarity being opposite the second polarity.
16. The neural interface of embodiment 15, wherein the first continuous strip, the second continuous strip, and the third continuous strip are embedded in the tube and recessed from the exterior surface of the tube.
17. The neural interface of embodiment 1, wherein the at least two electrodes include a first array of multiple electrodes and a second array of multiple electrodes, wherein each electrode in each of the first array and the second array are connected to a conductor among the plurality of conductors.
18. The neural interface of embodiment 17, wherein each electrode of the first array and the second array are independently configured to be selected and activated for power/current grading of a stimulation field around of the target vessel.
19. The neural interface of embodiment 17, wherein each electrode of the first array and the second array is configured to have a selective negative polarity or a selective positive polarity.
20. A method of manufacturing a neural interface, comprising:
 (a) laser ablating a plurality of cavities in an outer diameter of a tube including a plurality of lumen;
 (b) inserting a conductor into each lumen among the plurality of lumen;
 (c) connecting an electrode to a distal end of a conductor and positioning the electrode over a cavity among a plurality of cavities, wherein a first cavity among the plurality of cavities is near a proximate end of a distal length of the tube;
 (d) placing a spacer over the tube and positioning the spacer against a distal edge of the electrode;
 (e) repeating (c) and (d) until a last electrode among the plurality of electrodes is positioned in a corresponding last cavity;
 (f) melting the plurality of spacers and filling the plurality of cavities;
 (g) inserting an overlay over the distal length; and
 (h) thermoshaping the distal length in a helical shape.
21. The method of embodiment 20, wherein the plurality of electrodes are coil electrodes.
22. The method of embodiment 20, wherein the tube is a polyurethane multilumen tube.
23. The method of embodiment 20, wherein melting includes reflowing the tube.
24. The method of embodiment 23, wherein reflowing creates a distal end of the tube.
25. The method of embodiment 24, further comprising centerless grinding the distal end.
26. The method of embodiment 20, wherein the overlay is a silicone-based material, and wherein (g) includes solvent-swelling the overlay prior to inserting.
27. The method of embodiment 26, further comprising doping the silicone-based material with a steroid drug.
28. The method of embodiment 26, further comprising coating the silicone-based material with a hydrophilic polymer.
29. The method of embodiment 20, further comprising exposing the plurality of electrodes under the overlay by laser ablating openings in the overlay at desired locations.
30. The method of embodiment 20, wherein the helical shape is formed by a mandrel of a desired diameter and at desired helix angle for an intended application.

The embodiments of the present disclosure, while illustrated and described in terms of various embodiments, is not limited to the particular description contained in this specification. Additional alternative or equivalent components and elements may be readily used to practice the present disclosure.

What is claimed is:
1. A neural interface for interfacing with a target vessel, the neural interface comprising:
 a tube including a plurality of lumina within the tube and having a helical shape along at least part of the length of the tube;
 a plurality of conductors, wherein each conductor among the plurality of conductors is inserted into a corresponding lumen;
 at least two electrodes, wherein each electrode among the at least two electrodes is connected to a first end of a corresponding conductor and positioned at a position along the length of the tube so as to form no electrical transverse gap between electrodes over at least a 360 degree turn around an interior surface or an exterior surface of the target vessel when positioned in or on the target vessel; and
 an overlay positioned over the tube and the electrodes, the overlay including a plurality of openings exposing each conductor to the interior surface or the exterior surface of the target vessel.
2. The neural interface of claim 1, wherein the plurality of electrodes are positioned according to one of following:
 toward a surface of the tubing adjacent to the interior surface of the target vessel, when positioned in the target vessel; or
 toward a surface of the tubing adjacent to the exterior surface of the target vessel, when positioned on the target vessel.
3. The neural interface of claim 1, further comprising a plurality of spacers, wherein at least one spacer is positioned between adjacent electrodes among the plurality of electrodes, wherein the tube and the plurality of spacers are a polyurethane material, and wherein the polyurethane material is reflowed to melt the spacers, fill the laser ablation and create an end for the tube.

4. The neural interface of claim 3, wherein the end is centerless ground.

5. The neural interface of claim 1, wherein the position of the at least two electrodes is determined by a laser ablation in the surface of the tube.

6. The neural interface of claim 1, wherein the at least two electrodes are coil electrodes.

7. The neural interface of claim 1, wherein the overlay is a silicone-based material, and wherein the silicone-based material is at least one of:
    doped with a steroid drug; or
    coated with a hydrophilic polymer.

8. The neural interface of claim 1, wherein the helical shape includes at least one complete helical turn.

9. The neural interface of claim 1, wherein the at least two electrodes are a first continuous strip and a second continuous strip, and at least one of:
    the first continuous strip is configured to have a negative polarity and the second continuous strip is configured to have a positive polarity; or
    the first continuous strip and the second continuous strip are embedded in the tube and recessed from the exterior surface of the tube.

10. The neural interface of claim 1, wherein the at least two electrodes are a first continuous strip, a second continuous strip and a third continuous strip, at least one of:
    at least two continuous strips of the first continuous strip, the second continuous strip and the third continuous strip are configured to have a first polarity and a remaining continuous strip is configured to have a second polarity, the first polarity being opposite the second polarity; or
    the first continuous strip, the second continuous strip, and the third continuous strip are embedded in the tube and recessed from the exterior surface of the tube.

11. The neural interface of claim 1, wherein the at least two electrodes include a first array of multiple electrodes and a second array of multiple electrodes, and at least one of:
    each electrode in each of the first array and the second array are connected to a conductor among the plurality of conductors;
    each electrode of the first array and the second array are independently configured to be selected and activated for power/current grading of a stimulation field around of the target vessel; or
    each electrode of the first array and the second array is configured to have a selective negative polarity or a selective positive polarity.

* * * * *